United States Patent [19]
Zambias

[11] Patent Number: 5,430,018
[45] Date of Patent: Jul. 4, 1995

[54] CYCLOHEXAPEPTIDE WITH BASIC NITROGEN CONTAINING ALKYLAMIDE GROUPS

[75] Inventor: Robert A. Zambias, Springfield, N.J.

[73] Assignee: Merck & Co., Inc., Rahway, N.J.

[21] Appl. No.: 775,774

[22] Filed: Oct. 17, 1991

[51] Int. Cl.$^6$ .................... A61K 37/02; C07K 7/50
[52] U.S. Cl. .......................... 514/11; 514/9;
  514/2; 530/317; 930/270; 930/DIG. 546;
  930/DIG. 548
[58] Field of Search ............... 514/11, 9, 2; 530/317;
  930/270, DIG. 546, DIG. 548

[56] References Cited

U.S. PATENT DOCUMENTS

| | | | |
|---|---|---|---|
| 4,287,120 | 9/1981 | Abbott et al. | 530/317 |
| 4,293,489 | 10/1981 | Debono | 530/317 |
| 4,320,053 | 3/1982 | Abbott et al. | 530/317 |
| 4,931,352 | 6/1990 | Fromtling et al. | 530/317 |
| 4,968,608 | 11/1990 | Giacobbe et al. | 530/317 |
| 5,021,341 | 6/1991 | Giacobbe et al. | 530/317 |
| 5,021,403 | 6/1991 | Sesin et al. | 530/317 |
| 5,049,546 | 9/1991 | Sesin et al. | 530/317 |
| 5,166,135 | 11/1992 | Schmatz | 514/11 |

FOREIGN PATENT DOCUMENTS

| | | |
|---|---|---|
| 0448354 | 3/1991 | European Pat. Off. . |
| 0448343 | 9/1991 | European Pat. Off. . |
| 0448353 | 9/1991 | European Pat. Off. . |
| 0448356 | 9/1991 | European Pat. Off. . |
| 93302064 | 9/1993 | European Pat. Off. . |
| 2-288837 | 11/1990 | Japan . |

OTHER PUBLICATIONS

Bartlett, M. S., et al. Clin. Microbiol. Rev. 4(2):137–149 (Apr. 1991).
Gautier, V., et al. Clin, Exp. Allergy 21:63–66 (1991).
Henson, J. W., et al. Arch Neurol. 48: 406–409 (Apr. 1991).
Jacobs, J. L., et al. N. Eng. J. Med. 324(4): 246–250 (1991).
Pavlica, F. Ann. paeadiat. 198: 177–184 (1962).
Poplin, E. A., et al. Cancer 68: 193–194 (1991).
Sepkowitz, K. A., et al. JAMA 267(6): 832–837 (1992).
Schmatz, D. M., et al. Workshop on Pneumocystis, Cryptosporidium and Microsporidia supp. to J. Protozoology 38(6): 151S–151S (Nov.–Dec. 1991).
Schmatz, D. M., et al. Antimicrobial Agents and Chemo. 36(9): 1964–1970 (1992).
Varthalitis, I., et al. Cancer 71(12): 481–485 (1993).
Walzer, P. D., et al. Diagn. Microbiol. Infect. Dis. 2: 1–6 (1984).
Walzer, P. D. N. Eng. J. Med. 324(4): 263–265 (1991).
Zambias, et al. J. Med. Chem. 35(15): 2843–2855 (1992).
The Merck Manual of Diagnosis and Therapy, 11th ed., pp. 885–891, (1966).

*Primary Examiner*—Jill Warden
*Assistant Examiner*—T. D. Wessencorf
*Attorney, Agent, or Firm*—Elliott Korsen; Mark R. Daniel

[57] ABSTRACT

Certain aminoalkyl substituted amides which have a cyclohexapeptidyl group and which are found to have antibiotic activity with physical properties suitable for use in therapeutic compositions are described.

16 Claims, No Drawings

SEQUENCE LISTING ( 1 ) GENERAL INFORMATION:

( i i i ) NUMBER OF SEQUENCES: 4

( 2 ) INFORMATION FOR SEQ ID NO: 1:

( i ) SEQUENCE CHARACTERISTICS:
( A ) LENGTH: 6
( B ) TYPE: AMINO ACID
( C ) STRANDEDNESS: NA
( D ) TOPOLOGY: CIRCULAR ( i i ) MOLECULE TYPE:
( A ) DESCRIPTION: PEPTIDE ( x i ) SEQUENCE DESCRIPTION: SEQ ID NO: 1:

```
        Xaa  Thr  Xaa  Xaa  Xaa  Xaa
         1                 5
```

( 2 ) INFORMATION FOR SEQ ID NO: 2:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 2:

```
        Xaa  Thr  Xaa  Xaa  Xaa  Xaa
         1                 5
```

( 2 ) INFORMATION FOR SEQ ID NO: 3:

( i ) SEQUENCE CHARACTERISTICS:
        ( A ) LENGTH: 6
        ( B ) TYPE: AMINO ACID
        ( C ) STRANDEDNESS: NA
        ( D ) TOPOLOGY: CIRCULAR ( i i ) MOLECULE TYPE:
        ( A ) DESCRIPTION: PEPTIDE ( x i ) SEQUENCE DESCRIPTION: SEQ ID NO: 3:

```
        Xaa  Thr  Xaa  Xaa  Xaa  Xaa
         1                 5
```

CYCLOHEXAPEPTIDE WITH BASIC NITROGEN CONTAINING ALKYLAMIDE GROUPS

The present invention is directed to certain aminoalkyl substituted amides and acid addition salts thereof.

The aminoalkyl-substituted amides of the present invention are amides of β-hydroxypropionic acid which also have a cyclohexapeptidyl substituent at the β-position of the acid and may be represented by the formula (Seq. ID Nos. 1-3):

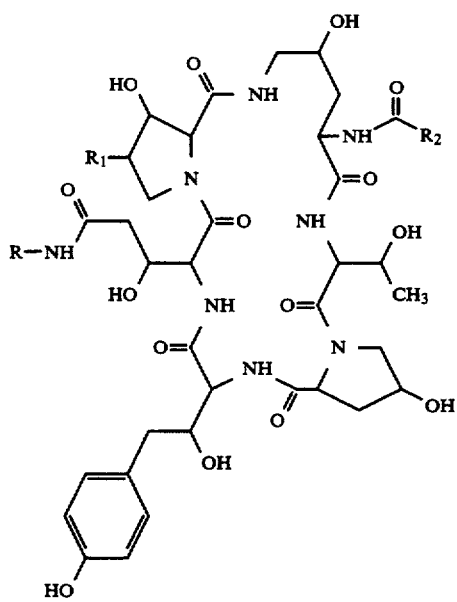

(A)

In this and succeeding formulas, $R_1$ is H, OH or $CH_3$ $R_2$ is $C_9-C_{21}$ alkyl, $C_9-C_{21}$ alkenyl or $C_1-C_{10}$ alkoxyphenyl, R is X-A- where A is an aliphatic link from 2 to 6 carbon units in length and may contain a neutral group, or a group forming a zwitterion with the basic nitrogen; and X is a basic amine group.

When "alkyl", "alkenyl" or "alkoxy" is employed, it is intended to include branched as well as straight chain radicals.

By "basic amine group" is meant either substituted or unsubstituted amino nitrogen or a group which contains in its structure a basic nitrogen which is connected through a non-aromatic carbon chain to the amide group in the formula.

"X" may be further defined as follows:
X is

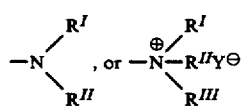

where $R^I$, $R^{II}$ and $R^{III}$ are independently H or lower alkyl ($C_1$-$C_4$), and $Y^-$ is an anion of a pharmaceutically acceptable salt;

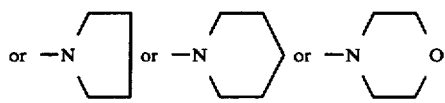

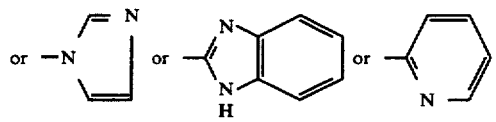

A is preferably alkylene from 2 to 6 carbon atoms. Also "X-A" may be an integral unit such as

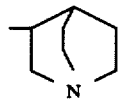

The neutral or zwitterion forming acid groups which optionally may be present on the non-aromatic chain include carboxyl, hydroxyl, ether or ester.

Pharmaceutically acceptable salts suitable as acid addition salts as well as salts providing the anion of the quaternary salt are those from acids such as hydrochloric, hydrobromic, phosphoric, sulfuric, maleic, citric, acetic, tartaric, succinic, oxalic, malic, glutamic and the like, and include other acids related to the pharmaceutically acceptable salts listed in Journal of Pharmaceutical Science, 66, 2 (1977).

Representative nuclei for the aminoalkylamide compounds, Compound A, and the sequence ID for these compounds may be seen in the following table.

| Amide | $R_1$ | SEQ. ID NO. |
|---|---|---|
| A-1 | H | 1 |
| A-2 | $CH_3$ | 2 |
| A-3 | OH | 3 |

Since the amino acid nuclei would be the same irrespective of the substituents R and $R_2$, the sequence ID numbers would be the same for many of the compounds since the variation in many of the compounds are in the side chain and is not changing the amino acid of the peptide.

The preferred compounds of the present invention are those in which $R_1$ is H, $R_2$ is 9,11-dimethyltridecyl (DMTD) and which may be described by the following formula:

(A-1) Seq. ID No. 1

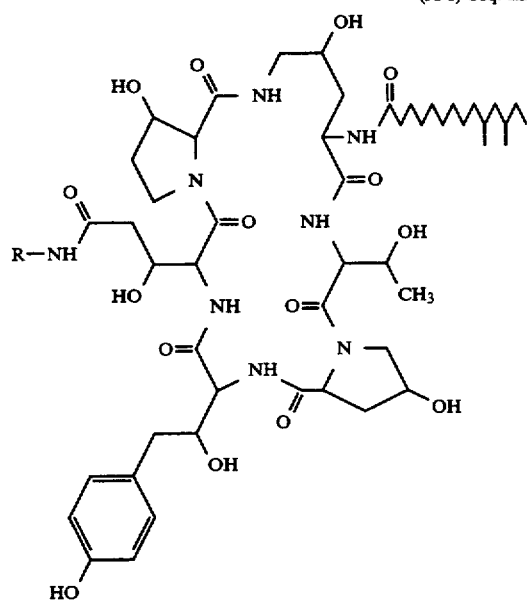

The compounds in which the cyclopeptidyl nucleus and the lipophilic side chain are as in the above formula will be represented by

R—(Z)

in which Z includes the cyclohexapeptidyl nucleus joined at the β-position of β-hydroxypropionamide and in which the α-amino nitrogen of 4-hydroxyornithine is substituted with the 10,12-dimethyltetradecanoyl (or 10,12-dimethylmyristoyl) radical.

The compounds are soluble in lower alcohols and polar aprotic solvents such as dimethylformamide (DMF), collidine and pyridine. They are insoluble in solvents such as ether and acetonitrile.

The compounds of the present invention are useful as an antibiotic, especially as an antifungal agent or as an antiprotozoal agent. As antifungal agents they are useful for the control of both filamentous fungi and yeasts. They are especially adaptable to be employed for the treatment of mycotic infections in mammals, especially those caused by Candida species such as C. albicans, C. tropicalis and C. pseudotropicalis. A number of the compounds are also useful for the treatment and/or prevention of Pneumocystis carinii pneumonia to which immune compromised patients are especially susceptible.

The compounds may be prepared through the sequence of reactions seen below in which a careful hydrolysis of a cyclohexapeptide produces an intermediate ester which may then be converted to the acid which in turn is condensed with an amine to obtain the amino substituted amides.

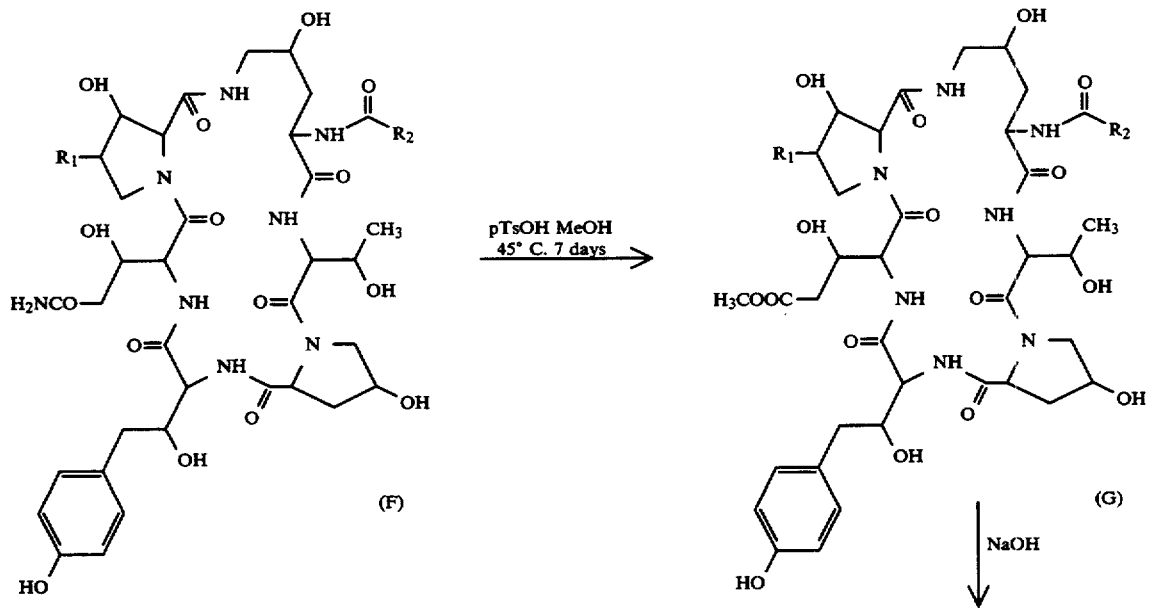

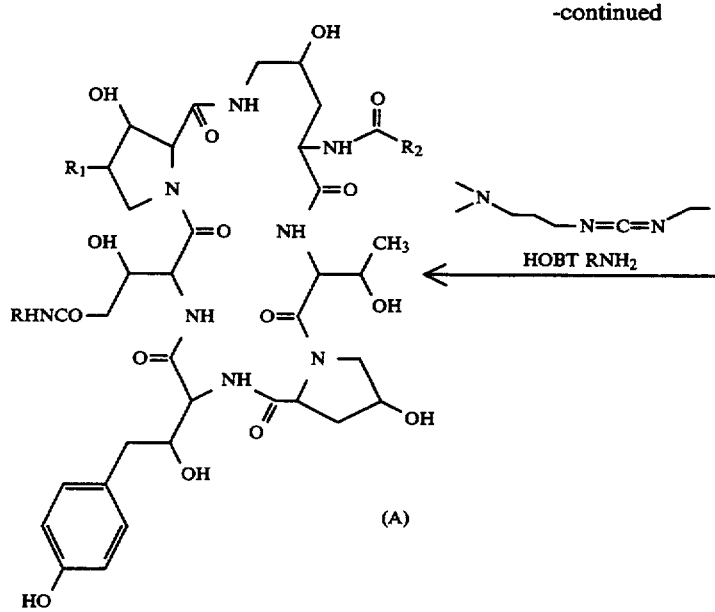

(A)

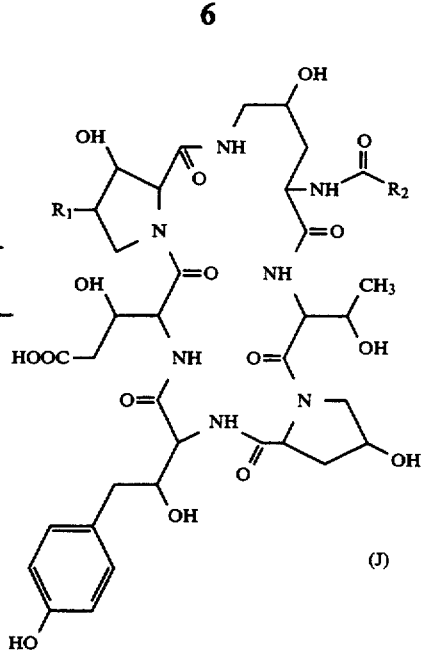

(J)

Since the change in the formula for the various new compounds of the present invention is at the same terminal position of the same amino acid component, and does not change the amino acid of the peptide, the various intermediates (F), (G) and (J) have the same sequence identification as the final product.

The cyclohexapeptide compound is replete with carboxamide groups, not only from the peptide linkage, but from the acyl link on the α-aminonitrogen of the ornithine component and the amide group from the glutamine component of the peptide. Thus, the hydrolysis of the glutamine component must be carefully controlled. Under mild conditions, in the presence of an alcohol, alcoholysis may be made to occur with the formation of an ester.

The acid to be used for the alcoholysis is preferably p-toluene sulfonic acid (pTs OH). However, other strong acids may be employed such as hydrochloric, sulfuric, camphorsulfonic acid and the like.

For the purpose of preparing the ester as an intermediate, methanol is satisfactory. Both methyl ester and higher esters (Q instead of $CH_3$ in formula (G)) are novel compounds. No compound is known with an ester group in that position.

The free acid then may be produced from the ester by the saponification reaction. The saponification is carried out conveniently at ambient temperature. Generally, the ester intermediate is suspended in the alcohol and the alkali added. About two equivalents of the base in the concentration range of 1.5 N to 2.5 N are employed, The reaction is substantially instantaneous with the formation of the desired acid in the salt form. The salt may be converted to the carboxyl form by conventional procedures. It is conveniently carried out by diluting the alkaline solution with water and adding a strong acid such as trifluoroacetic acid. The acid may be purified by preparative HPLC eluting isocratically with acetonitrile/water.

In this purification procedure as well as in assay methods, the mobile phase used are varying ratios of a water/acetonitrile composition and an acetonitrile/water composition. These compositions are referred to in the examples as compositions A and B. In composition A, the ratio is 95/5 water/acetonitrile. In composition B, the ratio is 95/5 acetonitrile/water. Both A and B may also contain either 0.1% TFA or 0.1% acetic acid. The exact composition, i.e., the ratio of A to B, to be employed in an assay procedure and that to be employed in preparative HPLC may differ not only from each other but from compound to compound but can be determined by the skilled artisan without difficulty.

The column generally employed for assay is "ZORBAX" (DuPont) C8 (4.5 mm × 25 cm) and is used with appropriate ratios of A:B at a flow rate of 1.5 ml/min. at 40° C. with ultraviolet detection at λ210 mµ.

The column employed for preparative HPLC may be "ZORBAX" C8 of 25 cm with I.D. from 10 mm to 25 mm, and the columns may be employed in a series of two. Alternatively, it may be a Δ-PAK C18 (25 mm × 10 cm) radial cartridge.

The acid obtained is then caused to react with $RNH_2$ which is an aliphatic amine having at least one primary amino group and a second non-aromatic amino group which may be primary, secondary, tertiary or quaternary. The two basic nitrogens are joined through a link which need not be a simple alkylene chain although generally such is the case.

The acylation reaction is then carried out by adding the his amine, hydroxybenzotriazole (HOBT) and dimethylaminopropyl ethyl carbodiimide hydrochloride or other suitable dehydrating reagent to a solution (in some cases, suspension) of the acid in an aprotic solvent, generally in an atmosphere of nitrogen for from about one to thirty hours. As a result of these operations, the desired product, Compound A, is formed in the reaction mixture. The product may be recovered by preparative high performance liquid chromatography (HPLC). The fractions containing the desired product may be concentrated and lyophilized.

Depending on the nature of R, other procedures may be employed after the foregoing, such as for example, reductive removal of a protective group such as carbobenzyloxy. Such procedures are well-known and are described where applicable in the working examples.

The compounds of the present invention are active against many fungi and particularly against Candida species. The antifungal properties maybe illustrated with the minimum fungicidal concentration (MFC) determination against certain Candida organisms in a microbroth dilution assay carried out in a Yeast Nitrogen Base (Difco) medium with 1% dextrose (YNBD).

In separate assays, the compounds (all Seq. ID No. 1) were solubilized in 10% dimethyl sulfoxide (DMSO) and diluted to 2560 µg/ml. The solution was then diluted to 256 µg/ml in YNBD and dispensed via a multichannel pipetter into the top row of a 96-well plate (each well containing 0.15 ml of YNBD), resulting in a drug concentration of 128 µg/ml. Compounds in the top row were diluted 2-fold down the columns yielding final drug concentrations ranging from 128–0.06 µg/ml. All tests were performed in duplicate.

A four-hour broth culture of *C. albicans* MY 1055 was adjusted using a spectrophotometer at 530 nm to equal a 0.5 McFarland Standard. This yields a cell concentration of $1-5 \times 10^6$ colony forming units (CFU)/ml. The 96-well microplates were inoculated using an MIC-2000 (Dynatech), which delivers 1.5 µg per well, yielding a final inoculum per well of $1.5-7.5 \times 10^3$ cells. One column per tray containing drug-free growth control wells was included.

After 24 hours of incubation, the microtiter plates were shaken gently on a shaker to resuspend the cells. The MIC-2000 inoculator was used to transfer a 1.5 microliter sample from each well of the 96-well microtiter plate to a single reservoir inoculum plate containing Sabouraud dextrose agar (SDA). The inoculated SDA plates were incubated for 24 hours at 35° C. The results were as seen in the following table:
(All compounds are of the type A-1 having Sequence ID No. 1. The compounds are identified by formula number which corresponds to the working examples.)

| | MFC µg/mL | |
|---|---|---|
| Compound | C. albicans MY 1055 | C. albicans MY 1028 |
| I | 2 | <0.06 |
| II | 0.25 | 0.25 |
| III | 0.125 | 0.25 |
| IV | 0.25 | <0.06 |
| V | 0.25 | 0.125 |
| VI | 0.125 | 0.125 |
| VII | 6.5 | 16 |
| VIII | 2 | 0.5 |

The starting acid and ester also show activity against *Candida albicans*. Thus, the acid showed MFC against *C. albicans* MY 1055 and MY 1028 of 0.5 µg/mL and 1 µg/mL, respectively and the methyl ester showed MFC against *C. albicans* MY 1055 and MY 1028 of 0.5 µg/mL and 0.25 µg/mL respectively.

The compounds of the present invention may also be useful for inhibiting or alleviating *Pneumocystis carinii* infections in immune compromised patients. The efficacy of the compounds of the present invention for therapeutic or anti-infective purposes may be demonstrated in studies on immunosuppressed rats in which Sprague-Dawley rats (weighing approximately 250 grams) are immunosuppressed with dexasone in the drinking water (2.0 mg/L) and maintained on a low protein diet for seven weeks to induce the development of pneumocystis pneumonia from a latent infection. Before drug treatment, two rats are sacrifaced to confirm the presence of *Pneumocystis carinii* pneumonia (PCP). Five rats (weighing approximately 150 grams) are injected twice daily for four days subcutaneously (sc) with Compound A in 0.25 ml of vehicle (distilled water). A vehicle control is also carried out. All animals continue to receive dexasone in the drinking water and low protein diet during the treatment period. At the completion of the treatment, all animals are sacrificed, the lungs are removed and processed, and the extent of disease determined by microscopic examination of stained slides for the presence of cysts. The prevention of or reduction of cysts may be seen when slides of lungs of treated rats are compared with slides lungs of untreated controls or solvent controls.

The outstanding properties are most effectively utilized when the compound is formulated into novel pharmaceutical compositions with a pharmaceutically acceptable carrier according to conventional pharmaceutical compounding techniques.

The novel compositions contain at least a therapeutic antifungal or antipneumocystis amount of the active compound. Generally, the composition contains at least 1% by weight of Compound A or one of the components. Concentrate compositions suitable for dilutions prior to use may contain 90% or more by weight. The compositions include compositions suitable for oral, topical, parenteral (including intraperitoneal, subcutaneous, intramuscular, and intravenous), nasal, and suppository administration, or insufflation. The compositions may be prepacked by intimately mixing Compound A with the components suitable for the medium desired. Compositions formulated for oral administration may be a liquid composition or a solid composition. For liquid preparations, the therapeutic agent may be formulated with liquid carriers such as water, glycols, oils, alcohols, and the like, and for solid preparations such as capsules and tablets, with solid carriers such as starches, sugars, kaolin, ethyl cellulose, calcium and sodium carbonate, calcium phosphate, kaolin, talc, lactose, generally with lubricant such as calcium stearate, together with binders disintegrating agents and the like. Because of their ease in administration, tablets and capsules represent the most advantageous oral dosage form. It is especially advantageous to formulate the compositions in unit dosage form (as hereinafter defined) for ease of administration and uniformity of dosage. Compositions in unit dosage form constitute an aspect of the present invention. Compositions may be formulated for injection and for injection take such forms as suspensions, solutions or emulsions in oily or aqueous vehicles such as 0.85 percent sodium chloride or 5 percent dextrose in water and may contain formulating agents such as suspending, stabilizing and/or dispersing agents. Buffering agents as well as additives such as saline or glucose may be added to make the solutions isotonic. The compound also may be solubilized in alcohol/propylene glycol or polyethylene glycol for drip intravenous administration. These compositions also may be presented in unit dosage form in ampoules or in multidose containers, preferably with added preservative. Alternatively, the active ingredients may be in powder form for reconstituting with a suitable vehicle prior to administration.

The term "unit dosage form" as used in the specification and claims refer to physically discrete units, each unit containing a predetermined quantity of active ingredient calculated to produce the desired therapeutic effect in association with the pharmaceutical carrier. Examples of such unit dosage forms are tablets, capsules, pills, powder packets, wafers, measured unite in ampoules or in multidose containers and the like. A unit dosage of the present invention will generally contain from 100 to 200 milligrams of one of the compounds.

When the compound is for antifungal use any method of administration may be employed. For treating mycotic infections, oral administration is frequently preferred.

When the compound is to be employed for control of pneumocystis infections it is desirable to directly treat lung and bronchi. For this reason inhalation methods are preferred. For administration by inhalation, the compounds of the present invention are conveniently delivered in the form of an aerosol spray presentation from pressurized packs or nebulisers. The preferred delivery system for inhalation is a metered dose inhalation (MDI) aerosol, which may be formulated as a suspension or solution of one of the compounds in suitable propellants, such as fluorocarbons or hydrocarbons.

Although the compounds of the present invention may be employed as tablets, capsules, topical compositions, insufflation powders, suppositories and the like, the solubility of the compounds of the present invention in water and aqueous media render them adaptable for use in injectible formulations and also in liquid compositions suitable for aerosol sprays.

The following examples illustrate the invention but are not to be construed as limiting.

EXAMPLE A

Preparation of the Acid (Compound J)

This example illustrates the preparation of the acid with a compound in which $R_1$ is H and $R_2$ is 9,11-dimethyltridecyl.

Part A. Methyl Ester (G)

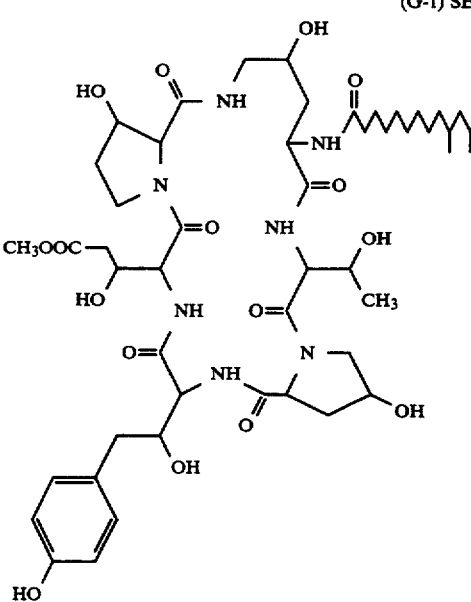

(G-1) SEQ. ID No. 1

To a solution of 2.5 grams of Compound F ($R_1$ is H; $R_2$ is DMTD) in 100 milliliters of methanol was added 500 milligrams of p-toluenesulfonic acid. The resulting solution was sealed and heated to 45° C., for 11 days. HPLC analysis ("ZORBAX" C8 4.9 mm×25cm; mobile phase 45/55 A/B (0.1% TFA); flow=1.5 ml/min; 40° C.; monitored at λ=210 nm) showed a ratio of 5.2:1 of product to starting material. The reaction mixture was diluted with 100 milliliters of water and injected onto a 45 mm 10 micron Δ PAK C18 radial compression column and then eluted first with 50/50 A/B at 20mL/min until the starting material was eluted. Then, the gradient was changed to 30/70 A/B at 60 mL/min. After the product was eluted the pure fractions as determined by HPLC were combined, then concentrated under reduced pressure and lyophilized to obtain 300 milligrams (12 percent) of the methyl ester (G-1) (Seq. ID No. 1). The methyl ester had the following spectral characteristics:

H NMR (400 MHz, CD$_3$OD): δ7.00 (d, 2H), 6.69 (d, H), 5.17 (d, 1H), 4.96 (d, 1H), 4.66 (dd, 1H), 4.58 (bs, 1H), 4.31 (m, 1H), 4.22 (d, 1H), 4.03 (dd, 1H), 3.66 (s, 3H), 2.96 (dd, 1H), 2.07 (td, 1H), 1.80 (m, 1H), 1.18 (d, 3H). Mass spectra (FAB): 1053 (M+Li )

Part B. Acid (J)

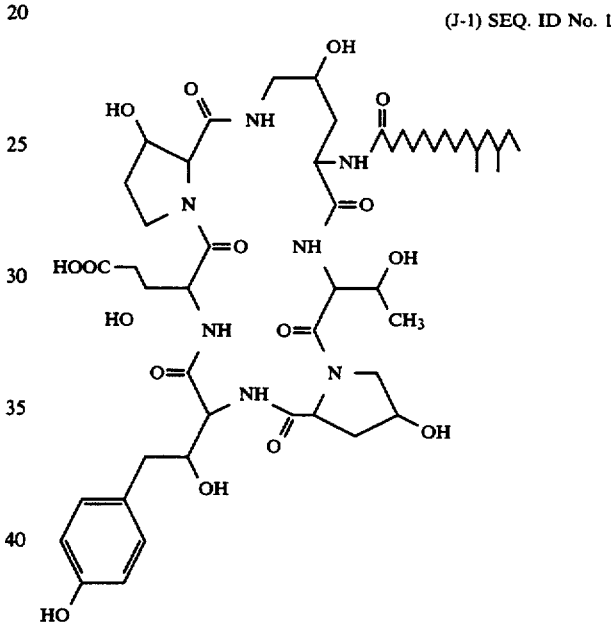

(J-1) SEQ. ID No. 1

T a suspension of 500 milligrams of the ester in 2.0 milliliters of methanol was added at room temperature, 500 microliters of 2N sodium hydroxide in methanol. A reaction took place immediately with the reaction mixture turning yellow in color. After HPLC assay of the reaction mixture, an additional 50 microliters of sodium hydroxide was added and the reaction continued at room temperature with stirring for seven hours. At the end of this period, the reaction mixture was diluted with 1.0 milliliter of water and the solution rendered acidic with trifluoroacetic acid. The solution was filtered and injected onto two "ZORBAX" C8 (22 mm id) columns in series and eluted isocratically with 50/50 A/B containing 0.1 percent TFA at 20.0 ml/min. The product, which by HPLC analysis was of >97.7% purity, was lyophilized overnight to obtain 325 milligrams, 66 percent, of the desired acid of formula (J-1) seq ID No 1:. The acid had the following spectral characteristics:

$^1$H NMR (400 MHz, CD$_3$OD): δ7.02 (d, 2H), 6.69 (d, 2H), 5.18 (dd, 1H), 4.97 (dd, 1H), 4.66 (dd, 1H), 4.58 (bs, 1H), 4.30 (m, 1H), 4.24 (d, 1H), 4.03 (dd, 1H), 2.96 (dd, 1H), 2.07 (td, 1H), 1.80 (m, 1H), 1.18 (d, 3H);

Mass spectra (FAB): 1039 (M+Li), 1046 (M+2Li)

EXAMPLE I

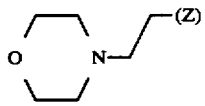
(I) Seq. ID No. 1

To a degassed solution of 50.6 milligrams (49 micromoles) of Acid Compound J-1 obtained in the manner described in Example A was added 10.6 milligrams (103 micromoles) of 4-(2-aminoethyl)morpholine followed first by 13.2 milligrams (98 micromoles) of hydroxybenzotriazole monohydrate, and then by 18.8 milligrams (98 micromoles) of dimethylaminopropylethylcarbodiimide hydrochloride and the mixture was stirred at room temperature under an atmosphere of nitrogen. After 0.5 hours, an HPLC analysis ("ZORBAX" C8, 4.5 mm×25 cm; 45/55 A/B; λ210 mμ) on the reaction mixture indicated substantial completion of the reaction. The reaction mixture was diluted with 1.0 milliliters of mobile phase (as used for analysis) and then injected onto a 10 mm×25 cm "ZORBAX" C8 column and eluted at 6.0 ml/min with A/B 45/55 but separation was not achieved under these conditions so the fractions were extracted onto a 1 inch "ZORBAX" C8 column and eluted 45/55 A/B containing 0.1% TFA to obtain 31 milligrams of the desired product as a trifluoroacetic acid salt.

The spectral characteristics of the product were as follows:

$^1$H NMR (400 MHz, CD$_3$OD): δ7.05 (d, 2H), 6.72 (d, H), 5.18 (d, 1H), 4.95 (bs, 1H), 4.66 (dd, 1H), 2.95 (bd, 1H), 2.66 (dd, 1H), 1.16 (d, 3H).

Mass spectra (FAB): 1146 (M+1), 1151 (M+Li).

EXAMPLE II

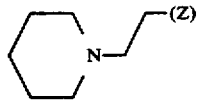
(II) Seq. ID No. 1

To a solution of 75 milligrams (73 micromole) of the acid (Compound J-1) prepared as described in Example A was added 19.7 milligrams (153.3 micromole) of 1-(2-aminoethyl)piperidine followed by 19.7 milligrams (146 micromoles) of HOBT monohydrate, and finally 28 milligrams (146 micromoles) of dimethylaminopropyl ethyl carbodiimide hydrochloride and the resulting mixture was stirred at room temperature for 1.5 hours. An HPLC analysis carried out at this time using "ZORBAX" C8 column (4.9 mm×25 cm) and eluting isocratically at 1.5 ml/min. with 45/55 A:B [composition containing 0.1% TFA] with temperature at 43° C. and reading at δ=210 nm. The analysis showed reaction to be complete. The product was injected into a Δ-PAK C18 column (25 mm×10 cm) and eluted with 45/55 A/B (compositions containing acetic acid) to obtain 60 milligrams of the compound of formula (I) as the acetate salt. The product had the following spectral data.

$^1$H NMR (400 MHz, CD$_3$OD): δ7.05 (d, 2H), 6.72 (d, 2H), 5.14 (d, 1H), 4.97 (d, 1H), 4.66 (dd, 1H), 2.63 (dd, 1H), 1.16 (d, 3H).

Mass spectra (FAB): 1144(M+1), 1150 (M+Li).

EXAMPLE III

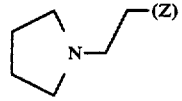
(III) Seq. ID No. 1

To a solution 75 milligrams of the acid of formula (J-1) (prepared as described in Example I) in 750 microliters of DMF was added 17.5 milligrams (153.3 micromoles) of 1-(2-aminoethylpyrrolidine) followed by 19.7 milligrams (146 micromoles) of HOBT monohydrate and finally by 28 milligrams (146 micromoles) of dimethylaminopropyl ethyl carbodiimide hydrochloride and the resulting mixture stirred for one hour. The reaction mixture was then diluted with 60/40 A/B (both in 0.1% acetic acid) mobile phase for preparative HPLC on Δ-PAK C18 column (25 mm×10 cm), injected onto the column and eluted at a flow rate of 8.4 milliliters per minute to obtain 40.0 milligrams of the desired product of formula (III). The compound had the following spectral characteristics:

$^1$H NMR (400 MHz, CD$_3$OD): δ7.04 (d, 2H), 6.70 (d, 2H), 5.13 (d, 1H), 4.65 (dd, 1H), 1.16 (d, 3H).

Mass spectra (FAB): 1136 (M+Li)

EXAMPLE IV

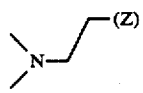
(IV) Seq. ID No.

To a solution of 150 milligrams (146 micromole) of Acid Compound (J-1) (obtained in the manner described in Example I) in 1.5 milliliters of DMF was added, under an atmosphere of nitrogen, 27 milligrams (307 micromoles) of N,N-dimethylethylenediamine, followed by 39 milligrams (292 micromoles) of HOBT monohydrate, and finally 56 milligrams (292 micromoles) of dimethylaminopropyl ethyl carbodiimide hydrochloride and the resulting mixture stirred at room temperature for one hour when it was determined that the reaction was complete by HPLC ["ZORBAX" C8; 45/55 A:B (0.1% TFA) at 1.5 ml/min.].

The reaction mixture was separated by HPLC by injecting onto a Δ-PAK C18 25 mm×10 cm radial compression column and eluted at 8 ml/min with 60/40 A/B (0.1% acetic acid). The fractions containing the product were combined and lyophilized to obtain 85 milligrams of crude product which was again purified by HPLC to obtain the desired product of formula IV as the acetic acid salt. The compound had the following spectral characteristics $^1$H NMR (400 MHz, CD$_3$OD): δ7.15 (d, 2H), 6.70 (d, 2H), 5.13 (d, 1H), 4.64 (dd, 1H), 4.27 (d, 1H), 2.65 (s, 6H), 1.18 (d, 3H).

Mass spectra (FAB): 1110 (M+Li).

EXAMPLE V

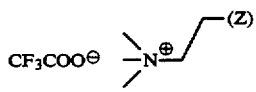
(V) Seq. ID No. 1

To a solution of the 40 milligrams (35.6 micromoles) of the dimethylamino compound (formula IV) prepared as described in Example IV) in 400 microliters of DMF was added 50.5 milligrams (356 micromoles) of methyl iodide under an atmosphere of nitrogen and the mixture stirred at room temperature for one hour. HPLC assay ["ZORBAX" C8; 45/55 A/B (0.1% TFA), at 1.5 ml/min, λ=210 mλ, T=40° C.] indicated the reaction was almost complete. Stirring was continued for another hour.

The reaction mixture was then injected onto the top of one of two "ZORBAX" C8 (25 mm ID) columns in series and eluted with the same mobile phase as above at 12.0 ml/min. and fractions collected. The desired product (Compound V) was recovered in the usual manner. The amount of product after purification was 31 milligrams as the trifluoroacetate salt. The compound had the following spectral characteristics:

$^1$H NMR (400 MHz, CD$_3$OD): δ7.05 (d, 2H), 6.69 (d, 2H), 5.09 (d, 1H), 4.95 (d, 1H), 4.65 (dd, 1H), 4.25 (d, 1H), 3.18 (s, 9H), 2.98 (d, 1H), 1.15 (d, 3H).
Mass spectrum (FAB): 1119 (M+1)

EXAMPLE VI

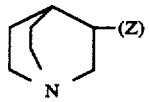
(VI) Seq. ID No. 1

To a solution of 75 milligrams (73 micromoles) of acid of formula (J-1) (prepared in the manner described in Example I), in 1.0 milliliters of DMF was added 31 milligrams (153.3 micromoles) of 3-aminoquinuclidine dihydrochloride, then 40 milligrams (306.6 micromoles) of diisopropylethylamine, followed by 19.7 milligrams (146 micromoles) of HOBT monohydrate, and finally 28 milligrams (146 micromoles) of dimethylaminopropyl ethyl carbodiimide hydrochloride and the mixture stirred at room temperature under nitrogen. HPLC assay ("ZORBAX" C8, 45/55 A/B 0.1% TFA at 1.5 ml/min., 40° C.) indicated substantial completion of the reaction. The reaction mixture was applied to two preparative "ZORBAX" C8 HPLC columns in series employing 50/50 A/B as mobile phase at a flow rate of 10 ml/min. Fractions of pure product and fractions needing recycle were collected. The fraction containing the pure product was lyophilized and amounted to 26 milligrams of product as TFA salt. The fractions needing recycling were rechromatographed and thereafter lyophilized to obtain the second diastereomer. The diastereomer had the following spectral properties:

$^1$H NMR (400 MHz, CD$_3$OD): δ7.02 (d, 2)t), 5.12 (m, 1H), 4.94 (d, 1H), 4.64 (dd, 1H), 4.30 (m, 1H), 4.24 (d, 1H), 4.16 (bm, 1H), 3.05 (dd, 1H), 2.98 (dd, 1H), 2.72 (dd, 1H), 1.15 (d, 3H).
Mass spectra (FAB): 1142 (M+1), 1148 (M+Li).

EXAMPLE VII

H$_2$N—(CH$_2$)$_6$—(Z)  (VII) Seq ID No 1

To a solution of 75 milligrams (73 micromole) of the acid (J-1) in 750 microliters of DMF was added under an atmosphere of nitrogen 34 milligrams (292 micromoles) of 1,6-hexanediamine followed by 19.7 milligrams (146 micromoles) of HOBT monohydrate and finally 28 milligrams (146 micromoles) of dimethylaminopropyl ethyl carbodiimide hydrochloride and the resulting mixture stirred at room temperature. After one hour, HPLC assay showed no reaction had occurred. Another 2 equivalents (28 mg) of carbodiimide and 2 equivalents (19.7 mg) of HOBT were added and the reaction mixture stirred overnight at room temperature under an atmosphere of nitrogen. HPLC assay showed reaction had occurred to produce a desired product which was isolated by preparative chromatography on two "ZORBAX" (21 mm ID) C8 columns in series eluting with 50/30 A/B at 10 ml/min. The pure fraction were pooled and lyophilized overnight to obtain 38 milligrams of the desired product (VII). The product had the following spectral characteristics:

$^1$H NMR (400 MHz, CD$_3$OD): δ7.02 (d, 2H), 6.68 (d, 2H), 5.09 (d, 1H), 4.64 (dd, 1H), 2.98 (dd, 1H), 2.90 (t, 2H), 2.74 (dd, 1H), 1.14 (d, 3H).
Mass spectra (FAB): 1138 (M+Li).

EXAMPLE VIII

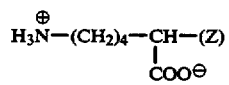
VIII Seq ID No 1

A. Preparation of the Intermediate Ester

To a solution of 75 milligrams (73 micromoles) of the acid (formula J-1) in 1.0 milliliter of DMF was added under nitrogen atmosphere, 62.4 milligrams (153.3 micromole) of ε-amino carbobenzyloxylysine benzyl ester hydrochloride, followed by 19.7 milligrams (153.3 micromole) of diisopropylethylamine, then by 19.7 milligrams (146 micromoles) of HOBT monohydrate, and finally by 28 milligrams of ethyl dimethylaminopropyl carbodiimide hydrochloride. After completion of the addition, the mixture was stirred at room temperature for two hours under nitrogen. The reaction mixture was injected onto two preparative "ZORBAX" C8 column (21 mm ID) in series and step-gradient elution performed from 50/50; 45/55; 40/60 and 30/70 A/B. The fractions containing product were combined to obtain 62 milligrams of the intermediate N-carbobenzyloxy benzyl ester.

B. Hydrogenation to Product 47 milligrams of the intermediate ester was dissolved in 1.0 milliliter of acetic acid and to it was added 10 milligrams of 10 percent palladium on carbon catalyst and hydrogenated at atmospheric pressure. After 3.5 hours, a check was made by HPLC. Some products had formed but an additional 2 milligrams of 10 percent Pd/C was added and hydrogenation continued overnight. The reaction mixture was applied to "ZORBAX" C8 and eluted with 5/55 A/B at 8.0 ml/min. The product fractions were combined and lyophilized overnight to obtain 16.5 milligrams of compound of formula VIII as a white amorphous solid. The compound had the following spectral properties.

$^1$H NMR (400 MHz, CD$_3$OD): δ7.02 (d, 2H), 6.70 (d, 2H), 5.12 (dd, 1H), 4.66 (dd, 1H), 4.58 (bs, 1H), 4.32 (m, 1H), 4.24 (d, 1H), 3.05 (dd, 1H), 2.98 (bd, 1H), 2.45 (m, 2H), 1.18 (d, 3H).
Mass spectra (FAB): 1168 (M+Li).

EXAMPLE IX

In a similar manner the following compounds were prepared:

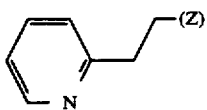

(A)

by the reaction of acid of formula (J-1) and 2-aminoethylpyridine. The product had the following spectral properties:
$^1$H NMR (400 MHz, CD$_3$OD): δ7.73 (td, 1H), 7.32 (d, 1H), 7.25 (td, 1H), 7.03 (d, 2H), 6.69 (d, 2H), 5.09 (m, 1H), 4.97 (d, 1H), 4.64 (dd, 1H), 2.70 (dd, 1H), 1.16 (d, 3H).
Mass spectra (FAB): 1144 (M+Li).

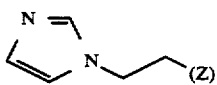

(B)

by the reaction of acid of formula (J-1) and 1-(3-aminopropyl)imidazole. The product had the following spectral properties:
$^1$H NMR (400 MHz, CD$_3$OD) δ6.99 (d, 2H), 6.69 (d, 2H), 5.10 (d, 1H), 4.96 (d, 1H), 4.64, (dd, 1H), 2.99 (dd, 1H), 2.63 (dd, 1H), 1.16 (d, 3H).
Mass spectra (FAB): 1147 (M+Li).

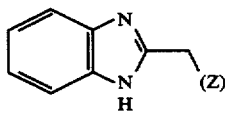

(C)

by the reaction of acid of formula (J-1) and 2-(aminomethyl)benzimidazole. The product had the following spectral properties
$^1$H NMR (400 MHz, CD$_3$OD): δ7.47 (m, 2H), 7.20 (m, 2H), 6.94 (d, 2H), 6.64 (d, 2H), 5.18 (m, 1H), 4.97 (d, 1H), 4.64 (dd, 1H), 2.99 (dd, 1H), 2.83 (dd, 1H), 1.13 (d, 3H).
Mass spectra (FAB): (M+1+Li).

EXAMPLE X

In a manner the following compounds are prepared:

| Compound | R$_1$ | R$_2$ |
|---|---|---|
| X-a | CH$_3$ | DMDT |
| X-b | CH$_3$ | (CH$_2$)$_7$CH=CH(CH$_2$)$_7$CH$_3$ |
| X-c | CH$_3$ | C$_6$H$_4$OC$_8$H$_{17}$ |
| X-d | OH | DMDT |
| X-e | OH | C$_6$H$_4$OC$_8$H$_{17}$ |
| X-f | OH | (CH$_2$)$_7$CH=CH(CH$_2$)$_7$CH$_3$ |

EXAMPLE XI 1000 compressed tablets each containing 500 mg of Compound I are prepared from the following formulation:

| Compound | Grams |
|---|---|
| Compound I (Seq. ID No. 1) | 500 |
| Starch | 750 |
| Dibasic calcium phosphate, hydrous | 5000 |
| Calcium stearate | 2.5 |

The finely powdered ingredients are mixed well and granulated with 10 percent starch paste. The granulation is dried and compressed into tablets.

EXAMPLE XII 1000 hard gelatin capsules, each containing 500 mg of Compound II are prepared from the following formulation:

| Compound | Grams |
|---|---|
| Compound II (Seq ID No 1) | 500 |
| Starch | 250 |
| Lactose | 750 |
| Talc | 250 |
| Calcium stearate | 10 |

A uniform mixture of the ingredients is prepared by blending and used to fill two-piece hard gelatin capsules.

EXAMPLE XIII

An aerosol composition may be prepared having the following formulation:

|  | Per Canister |
|---|---|
| Compound IV (Seq ID No 1) | 24 mg |
| Lecithin NF Liquid Concentrated | 1.2 mg |
| Trichlorofluoromethane, NF | 4.026 g |
| Dichlorodifluoromethane, NF | 12.15 g |

EXAMPLE XIV 250 milliliters of an injectible solution may be prepared by conventional procedures having the following formulation:

| | |
|---|---|
| Dextrose | 12.5 g |
| 26% aqueous polythylene glycol 300 | 250 ml |
| Compound VIII (Seq ID No 1) | 400 mg |

The ingredients are blended and thereafter sterilized for use.

Preparation of Starting Materials

The ultimate starting materials for compounds which are the starting materials for the series of reactions to obtain the products of the present invention are compounds which have been obtained by the reduction of the δ-hydroxyl in the ornithine component of a cyclohexapeptide having glutamine as one of the amino acid components according to the following equation.

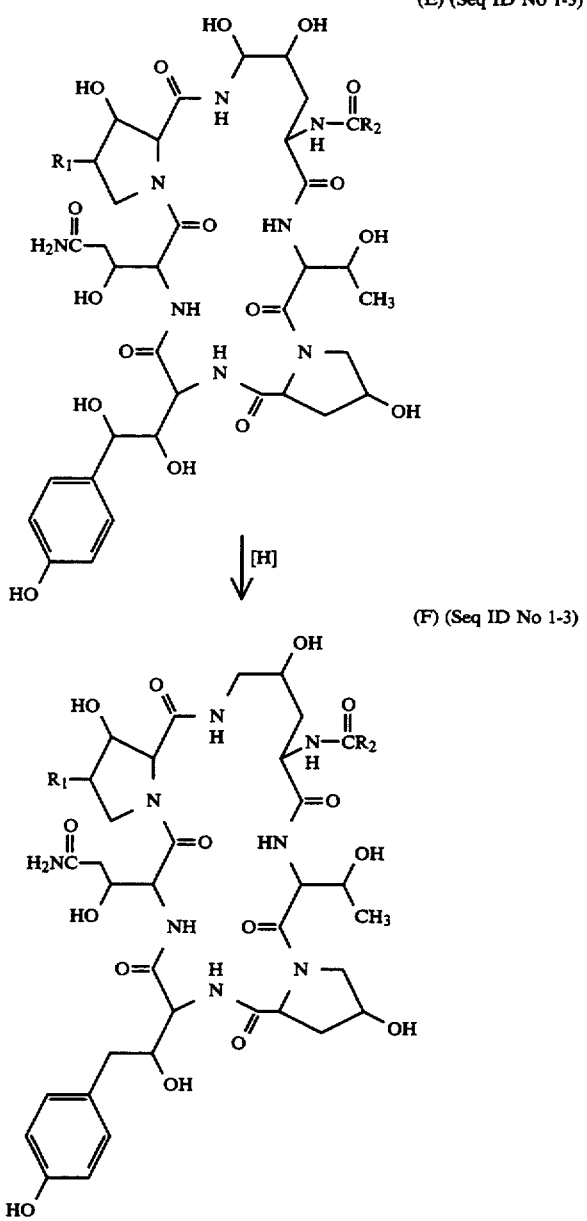

(E) (Seq ID No 1-3)

(F) (Seq ID No 1-3)

Compound of formula (E) represents two different natural products (when $R_1$ is H, Seq ID is 1; when $R_1$ is $CH_3$, Seq ID is 1). When $R_1$ is $CH_3$, it may be obtained by the fermentation of *Zalerion arboricola* ATCC 20868 in a nutrient medium as described in U.S. Pat. No. 4,931,352, Jun. 5, 1990, or in a nutrient medium enriched in glycerol as described in U.S. Pat. No. 4,968,608, Nov. 6, 1990.

When $R_1$ is H, it may be produced by cultivating *Z. arboricola* ATCC 20868 in a nutrient medium enriched in mannitol as the primary source of carbon as described in U.S. Pat. No. 5,021,341, Jun. 4, 1991.

When $R_1$ is OH, it may be produced by cultivating *Z. arboricola* ATOC 74030 in a nutrient medium containing assimilable sources of carbon, nitrogen and inorganic salts under aerobic conditions until a sufficient amount of the compound is produced and thereafter separating the product from the medium by extracting with alcohol and isolating the product by chromatographic separation.

(E) may be reduced to obtain (F) by intimately mixing (E) with a reducing agent such as sodium cyanoborohydride in the presence of a strong acid such as trifluoroacetic acid and the mixture stirred until the reaction is complete. The volatiles are then removed under reduced pressure and the residue purified by reverse phase chromatography employing water/acetonitrile to obtain the desired product.

What is claimed is:

1. A compound having the formula

[Chemical structure diagram of cyclic hexapeptide]

wherein
    $R_1$ is H, OH or $CH_3$,
    $R_2$ is $C_9$–$C_{21}$alkyl, $C_9$–$C_{21}$alkenyl, or $C_1$–$C_{10}$alkoxyphenyl,
    R is X-A wherein
        (a) A is an aliphatic link from 2 to 6 carbon units in length and which optionally contains a hydroxy, carboxy, ether or ester group, or a group forming a zwitterion with the basic nitrogen of X and X is a basic amine group selected from the group consisting of

[Structures: $-N(R^I)(R^{II})$ , or $-\overset{\oplus}{N}(R^I)(R^{II})(R^{III}) Y^{\ominus}$]

where
    $R^I$, $R^{II}$ and $R^{III}$ are independently H or lower ($C_1$-$C_4$) alkyl, and Y is an anion of a pharmaceutically acceptable salt,

[Structures: pyrrolidinyl, piperidinyl, morpholinyl, imidazolyl, benzimidazolyl and pyridyl ; or]

(b) X-A taken together is

[Quinuclidinyl structure]

2. A compound according to claim 1 in which R is

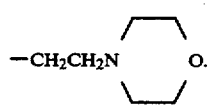

3. A compound according to claim 1 in which R is

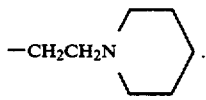

4. A compound according to claim 1 in which R is

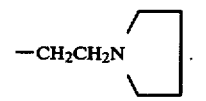

5. A compound according to claim 1 in which R is -CH$_2$CH$_2$N(CH$_3$)$_2$.

6. A compound according to claim 1 in which R is

7. A compound according to claim 1 in which R is

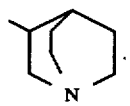

8. A compound according to claim 1 in which R is -(CH$_2$)$_6$-NH$_2$.

9. A compound according to claim 1 in which R is

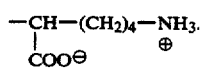

10. A compound according to claim 1 in which R is

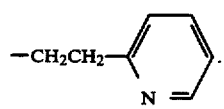

11. A compound according to claim 1 in which R is

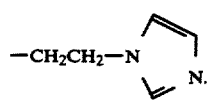

12. A compound according to claim 1 in which R is

13. An antibiotic composition comprising an antibiotic amount of a compound of claim 1 in a pharmaceutically acceptable carrier.

14. A composition according to claim 13 in unit dosage form wherein the compound of claim 1 is present in an amount of 10 milligrams to 200 milligrams.

15. A compound having the formula:

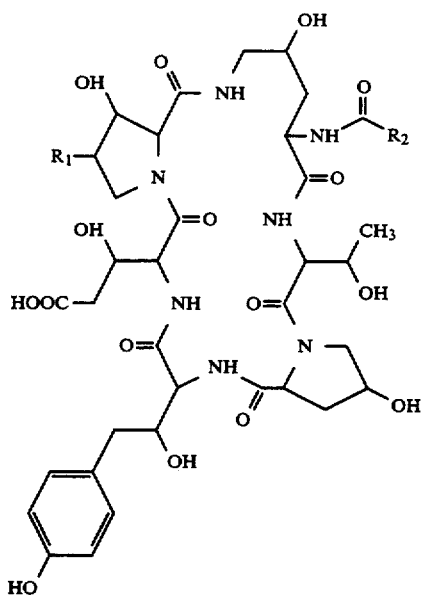

wherein R$_1$ and R$_2$ are as defined in claim 1.

16. A compound having the formula:

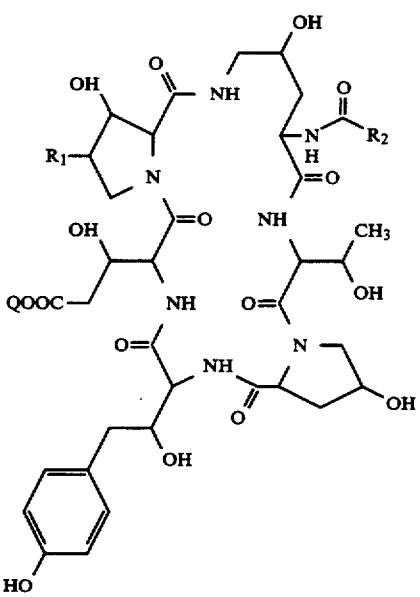

wherein R$_1$ and R$_2$ are as defined in claim 1 and Q is methyl.

* * * * *